(12) United States Patent
Price

(10) Patent No.: US 8,314,219 B1
(45) Date of Patent: Nov. 20, 2012

(54) GREEN DETERGENTS FROM AGRICULTURE-BASED LIPIDS AND SUGARS

(75) Inventor: Neil P Price, Edelstein, IL (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 128 days.

(21) Appl. No.: 12/777,588

(22) Filed: May 11, 2010

(51) Int. Cl.
| | |
|---|---|
| *C07H 5/04* | (2006.01) |
| *C07H 5/06* | (2006.01) |
| *C07H 1/00* | (2006.01) |
| *C07H 3/00* | (2006.01) |
| *C08B 37/00* | (2006.01) |

(52) U.S. Cl. .................. 536/18.7; 536/55.3; 536/124
(58) Field of Classification Search .............. 536/18.7, 536/55.3, 124
See application file for complete search history.

(56) References Cited

FOREIGN PATENT DOCUMENTS

WO WO2008042901 A2 4/2008

*Primary Examiner* — Eric S Olson
*Assistant Examiner* — Zhengfu Wang
(74) *Attorney, Agent, or Firm* — John Fado; Randall E. Deck; Lesley Shaw

(57) ABSTRACT

C-glycoside keto-amide derivatives, including C-glycoside keto-hydrazones and C-glycoside keto-oximes, may be prepared from plant or animal lipids and saccharides. These C-glycoside keto-amide derivatives are of the formula:

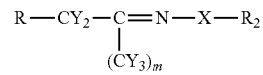

wherein:
R is a saccharide;
Y is independently selected from H or a halogen;
m is an integer greater than or equal to 1;
X is NH (as in C-glycoside keto-hydrazones) or O (as in C-glycoside keto-oximes); and
$R_2$ is an acyl moiety derived from any lipid fatty acid of the formula —C(O)—$R_3$, wherein $R_3$ is a C5 to C22 straight or branched chain hydrocarbon which may be saturated or unsaturated. These C-glycoside keto-amide derivatives have potential applications as surfactants, detergents, liposomes, and bilayers.

25 Claims, No Drawings

GREEN DETERGENTS FROM AGRICULTURE-BASED LIPIDS AND SUGARS

BACKGROUND OF THE INVENTION

1. Field of the Invention

The invention is drawn to novel C-glycoside keto-amide derivatives and methods for their production.

2. Description of the Prior Art

Numerous techniques for the derivatization of sugars have been described. Such techniques have included reductive amination and the formation of reducing sugar hydrazones, osazones, and oximes. However, in these techniques the integrity of the ring of the sugar is not retained but it is opened. The need therefore remains for improved process for preparing sugar derivatives wherein the ring of the sugar is not opened.

SUMMARY OF THE INVENTION

I have discovered novel C-glycoside keto-amide derivatives, including C-glycoside keto-hydrazones and C-glycoside keto-oximes, and methods for their preparation from plant or animal lipids and saccharides. These C-glycoside keto-amide derivatives are of the formula:

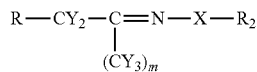

wherein:
R is a saccharide;
Y is independently selected from H or a halogen;
m is an integer greater than or equal to 1;
X is NH (as in C-glycoside keto-hydrazones) or O (as in C-glycoside keto-oximes) and $R_2$ is an acyl moiety derived from any lipid fatty acid of the formula —C(O)—$R_3$, wherein $R_3$ is a C5 to C22 straight or branched chain hydrocarbon which may be saturated or unsaturated. These C-glycoside keto-amide derivatives have potential applications as surfactants, detergents, liposomes, and bilayers.

The C-glycoside keto-amide derivatives of this invention may be produced in near quantitative yields from aqueous-based, one pot reactions. Furthermore, the functionalized C-glycosides retain the closed ring conformation of their parent sugars and no protecting group manipulations or activation of the anomeric center are needed. In one embodiment, the C-glycoside keto-amide derivatives may be produced by reacting a C-glycoside ketone with an acyl-linked ketone reactive compound, such as an acyl hydrazide (i.e., fatty acid hydrazide) or acyl β-hydroxylamine (i.e., fatty acid O-hydroxylamine), under conditions and for a period of time effective to produce a C-glycoside keto-amide derivative. The C-glycoside ketone and acyl-linked ketone reactive compound may be prepared from ordinary or known saccharides and fatty acids (including free fatty acids, their salts or esters and/or triglycerides) as starting materials, respectively. Preparation of the C-glycoside ketone may be effected by reacting an aldose reducing sugar, which may be a hexose or a pentose, with a β-diketone under conditions and for a period of time effective to form a C-glycoside ketone. The acyl-linked ketone reactive compound may be produced by reacting a lipid material containing the fatty acid or its ester with a ketone reactive compound, such as a hydrazine or hydroxylamine, under conditions and for a period of time effective to form the acyl (i.e., fatty acid) hydrazide or O-hydroxylamine.

In an alternative embodiment, C-glycoside keto-amide derivatives may be produced by first reacting a C-glycoside ketone with hydrazine or a salt thereof under conditions and for a period of time effective to produce a C-glycoside hydrazide. The C-glycoside hydrazide may then be reacted with a lipid containing a fatty acid ester (including free fatty acids, their salts or esters and/or triglycerides) under conditions and for a period of time effective to produce the C-glycoside keto-amide derivative.

In accordance with this discovery, it is an object of this invention to provide a process for making C-glycoside keto-amide derivatives from a variety of readily available saccharides and lipids, including free fatty acids or their esters, and preferably triglycerides and plant oils.

Another object of this invention is to provide a process for making C-glycoside keto-amide derivatives which are effective for use as surfactants, detergents, liposomes, and bilayers.

Still another object of this invention is to provide a process for making C-glycoside keto-amide derivatives wherein the ring structure of the sugar is not opened, but is retained without using any sugar protecting groups or activation.

Yet another object of this invention is to provide a process for making C-glycoside keto-amide derivatives under mild conditions in an aqueous solvent, and which is nearly quantitative.

Other objects and advantages of the invention will become readily apparent from the ensuing description.

DETAILED DESCRIPTION OF THE INVENTION

The C-glycoside keto-amide derivatives of this invention may be produced from a wide variety of lipids and sugars. Suitable lipids include any oils or fats (including those of plant or animal origin) which contain free fatty acids or their salts or their esters, including triglycerides. Potentially, any fatty acid (or triglyceride) can be used as the starting material, including those with different chain lengths (i.e., number of $CH_2$ groups), or saturated or unsaturated fatty acids (i.e., those with or without carbon/carbon double bonds). Hence it is possible to produce a broad variety of fatty acid hydrazide- or β-hydroxylamine-based detergents with potentially different cleaning properties (longer chain length detergents generally have improved surfactant properties). Thus, starting fatty acids include fatty acids of the formula $R_3$—$COOR_x$ wherein $R_3$ is a saturated or unsaturated, straight or branched chain hydrocarbon, and Rx is H or an alkali metal, branched or straight chain alkyl or alkenyl groups, aromatic containing groups, or glycerides (mono-, di- or triglyceride). It is also recognized that the $R_3$ moiety encompasses hydrocarbons which may be optionally substituted. Preferred starting fatty acids include, but are not limited to free and esterified fatty acids containing from 6 to 23 carbon atoms.

As starting materials in the reaction of the invention, the fatty acids may be provided in substantially pure form or, in the alternative, they may be provided as a mixture or in impure form. Moreover, although the starting unsaturated fatty acids may be free acids, the reaction may also be conducted using fatty acids which are esterified with aliphatic alcohols such as methanol, ethanol, isopropanol, or branched chain alcohols such as 2-ethyl hexanol or Guerbet alcohols, or with glycerol as mono-, di- or triglycerides. In a particularly preferred embodiment, because fatty acids occur predominantly as triglycerides in plant oils, naturally occurring oils may be used directly in the reaction, thereby foregoing the need for any preliminary fatty acid isolation of the oil. By way of example and without being limited thereto, suitable oils include soybean, cottonseed, corn, olive, peanut, palm, sesame, sunflower, canola, castor, safflower, linseed, oiticia, tung, rice, crambe, rape, and canola oils, with corn oil and olive oil being particularly preferred.

The practitioner skilled in the art will of course recognize that for products requiring a high degree of purity or uniformity, the oils may first be hydrolyzed to obtain free fatty acids for use as starting materials in the reaction. Hydrolysis of the oils to the fatty acids may be achieved using conventional splitting techniques or alkali splitting of fats. Suitable alkali splitting techniques include, for example, treatment with sodium methoxide, or sodium or potassium hydroxide [see "A.O.C.S. Tentative Method Ca 6b-53", in: Official and Tentative Methods of the American Oil Chemist's Society, third edition, AOCS, Chicago, Ill., (1973)]. Other conventional techniques including splitting with steam under pressure are also effective.

A similarly wide variety of saccharides are suitable for use in producing the C-glycoside keto-amide derivatives of this invention, and include any saccharides that contain an aldehyde-containing aldose reducing sugar, ranging from monosaccharides (such as glucose, xylose or arabinose), to disaccharides (such as lactose or cellobiose) and oligosaccharides (such as from starch, pectin sugars, and chitin sugars). Thus, the aldose sugar may be a simple hexose or pentose monosaccharide, or it may contain one or more substituent groups $R_1$ attached to any of the hydroxyl groups of the sugar. The $R_1$ substituents may be functional groups, including but not limited to hydroxyls, amines, O- or N-acyls such as N- or O-acetates or O-pyruvates, acid moieties such as carboxylates, phosphates or sulfates, or O-alkyls such as O-methyl, or glycosidally linked sugars, as described in greater detail hereinbelow. The structure of most typical aldose reducing sugars (i.e., six-member ring hexoses and five-member ring pentoses) used herein may generally be represented by the structure:

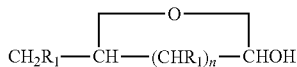

wherein n is 2 or 3, and $R_1$ at any of the C2, C3, C4, C5, and C6 carbons for hexoses, or at any of the C2, C3, C4, and C5 carbons for pentoses, are independently selected from one or more of the substituent groups described herein.

By way of example and without being limited thereto, specific examples of monosaccharides for use herein include:
1. Neutral aldohexoses, such as D-glucose, D-mannose, D-galactose, and the less common D-allose, D-altrose, D-gulose, D-idose, D-talose. The chemistry is also applicable to the less common L-series configuration of these sugars.
2. Neutral aldopentose, such as D-ribose, D-arabinose, D-xylose, and D-lyxose, and the corresponding L-series configuration.
3. N-acylamino-aldoses, such as N-acetyl-glucosamine (GlcNAc), N-acetyl-galactosamine (GalNAc), N-acetyl-mannosamine (ManNAc), and the corresponding free amino sugars, glucosamine (GlcN), galactosamine (GalN), and mannosamine (ManN). The chemistry is equally applicable to D- and L-configurations of these sugars. Also included in the group are muramic acid (MurN) and N-acetylmuramic acid (MurNAc), both important constituents of bacterial peptidoglycan.
4. Deoxy- and deoxyamino-substituted sugars. The chemistry is applicable to:—a) the important 2-deoxyaldopentose class of sugars, such as 2-deoxyribose (dRib), 2-deoxyarabinose, and 2-deoxyxylose; b) 6-deoxy-aldohexoses, such as D- and L-fucose (Fuc), D- and L-rhamnose (Rha), and quinovose (Qui); c) the corresponding amino sugars D-/L-fucosamines (FucN), D-/L-rhamnosamines (RhaN), and D/L-quinovosamines (QuiN); d) the 2-N-acetylated 6-deoxysugars, FucNAc, RhaNAc, and QuiNAc); e) other deoxysugars of commercial importance, including 2-deoxyaldoses such as 2-deoxyglucose (dGlc) which has the 2-hydroxyl group replaced by hydrogen, so that it cannot undergo metabolic glycolysis.
5. Methoxy-substituted sugars. The chemistry is applicable to ether-modified aldose (methoxy, ethoxy, benzyl, etc) sugars with a free anomeric position. Examples in this group are the non-metabolizable glucose analogs, 2-O-methyl-D-glucose, and 3-O-methyl-glucose, and the various partially methyl-substituted sugars used for carbohydrate linkage analysis. Others include 2-O-methylfucose, a common sugar in plant and bacterial cell walls, and 2-O-methylribose, a capping sugar for many ribonucleic acids (RNA).
6. Acidic uronic acid sugars and their salts, such as glucuronic acid (GlcA), galacturonic acid (GalA), and mannuronic acid (ManA). Also important in this category is L-iduronic acid (IdoA), a component of heparin and dermatan sulfate.

The process is also applicable to all classes of disaccharides and oligosaccharides that contain a terminal, aldehyde-containing aldose reducing sugar. Specific, non-limiting examples of oligosaccharides suitable for use as the saccharide starting materials include:
1. Oligosaccharides derived from hydrolysis of N-linked or O-linked glycoproteins. The oligosaccharides may be detached from the glycoproteins by acid or base hydrolysis, or by enzyme-catalyzed hydrolysis, that is, by processes that generate a free reducing sugar available for formation of the C-glycoside keto-amide derivatives. Important examples are the N-linked oligosaccharides (N-glycans) derived from immunoglobulins (antibodies), and other glycoproteins involved in biological recognition or adherence.
2. Oligosaccharides derived from blood group antigen glycans, that determine the ABO blood type specificity. The type O antigen acceptor substrate (H antigen) is Fuc alpha1→2 Gal-. Blood types A and B have two different oligosaccharide glycolipids embedded in the cell membranes of the red blood cells. Structures of A and B antigens are GalNAc alpha1→3 (Fuc alpha1→2) Gal-, and Gal alpha1→3 (Fuc alpha1→2) Gal-, respectively. The carbohydrate moiety of the ABH and Lewis glycoproteins consists primarily of four sugars, D-galactose, L-fucose, N-acetylgalactosamine and N-acetylglucosamine. Oligosaccharide chains are attached through an alkali-labile glycosidic bond to the hydroxyl group of serine or threonine. Most of the oligosaccharide chains are linked to the backbone through an N-acetylgalactosamine residue.
3. Oligosaccharides derived from tumor-associated antigens. Certain types of glycosphingolipids (GSL) are more highly expressed on the surfaces of tumor cells. Some of these tumor-associated antigens are adhesion molecules involved in tumor cell metastasis, tumor cell growth and motility, and have therefore been used to develop antitumor vaccines. Oligosaccharides derived from glycolipids and sphingolipids involved in adhesion and signaling are therefore targets for cancer therapy. Typical GSL antigens are the Lacto oligosaccharide series, $Le^x$, $Le^x$-$Le^x$, $Le^y$-$Le^x$, $Le^a$-$Le^a$, $SLe^x$, $SLe^x$-$Le^x$, and $SLe^a$, all of which terminate in lactose (Gal-beta1→4Glc at the reducing terminus. The lactose motif is highly applicable for the formation of C-glycoside ketohydrazones.
4. Oligosaccharides derived from hydrolysis of bacterial peptidoglycans, lipopolysaccharides, exopolysaccharides, techioc acids, or other microbial polysaccharides. The oligosaccharides may be detached from the corresponding bacterial polysaccharide, or bacterial or microbial cells by acid or base hydrolysis, or by enzyme-catalyzed hydrolysis; i.e. by processes that generate a free reducing sugar available for formation of the C-glycoside keto-amide derivatives.

5. Oligosaccharides derived from hydrolysis of glycosaminoglycans (GAGs) and proteoglycans. GAGs of physiological significance are hyaluronic acid, dermatan sulfate, chondroitin sulfate, heparin, heparin sulfate, and keratan sulfate. The linkage of GAGs to the proteoglycan core involves a specific trisaccharide composed of two galactose residues and a xylose residue (GAG-GalGalXyl-O—$CH_2$-protein). The GAGS are polysaccharides containing a repeating disaccharides unit composed N-acetylgalactosamine (GalNAc) or N-acetylglucosamine (GlcNAc) and a uronic acid such as glucuronate or iduronate, several of which are also sulfated. For example, heparin sulfate (HS) is a linear polysaccharide attached to the surface of nearly all mammalian cells. It consists of disaccharides repeats of glucuronic acid (GlcA) and N-acetyl-D-glucosamine (GlcNAc) with several modifications which can include N-deacetylation and N-sulfation of GlcNAc, epimerization of GlcA to L-iduronic acid (IdoA), 2-O sulfation of IdoA, and 6-O and 3-O sulfation of the glucosamine (GlcN). HS interact with fibroblast growth factor (FGF) and its receptor. Defective HS can cause loss of FGF and Hedgehog/Wingless signaling pathways, leading to severe abnormality in embryonic development, cell migration, and cancer cell metastasis. A well-defined physiological function of the GAG heparin is its role in preventing coagulation of the blood. In response to injury, heparin is released from the granules of mast cells that line blood vessels into the serum. Free heparin complexes with and activates antithrombin III, which in turn inhibits all the serine proteases of the coagulation cascade. This phenomenon has been clinically exploited in the use of heparin injection for anti-coagulation therapies.

6. Other miscellaneous oligosaccharides suitable for preparation of C-glycoside keto-amide derivatives are a) chitin oligosaccharides; b) prebiotic oligosaccharides, such as gentiooligosaccharide (GOS), xylooligosaccharides (XOS), and cellooligosaccharides (COS); and mannan oligosaccharides (MOS); c) oligosaccharides derived from plant cell wall components, such as pectin and hemicellulose; d) oligosaccharides derived from starch or maltodextrin, which have potential as inhibitors of beta-amylase; e) acarbose, beta-amylase inhibitor.

In addition to monosaccharides and oligosaccharides, the reactions of the invention may be used for the derivatization of phosphorylated and sulfated sugars (monosaccharides, disaccharides, oligosaccharides, or nucleic acids) that contain a terminal, aldehyde-containing aldose reducing sugars that may be optionally modified by an O- or N-linked substituent. The C-glycoside ketones and C-glycoside keto-hydrazones are readily prepared from these sugars in aqueous-based conditions and without the loss of the phosphate or sulfate groups. Specific examples include, but are not limited to:

1. Phosphorylated or sulfated monosaccharides. This includes 6-O-phosphorylated hexose monosaccharides, such as glucose-6-phosphate (Glc-6P), galactose-6-phosphate (Gal6P), N-acetylglucosamine-6-phosphate (GlcNAc-6P), mannose-6-phosphate (Man-6P), and 5-O-phosphorylated pentose monosaccharides, such as ribose-5-phosphate (Rib-5P), arabinose-5-phosphate (Ara-5P, and xylose-5-phosphate (Xyl-5P). Sulfated monosaccharides include N-acetylglucosamine-3-O-sulfate (GlcNAc-3S), and the O, N-sulfated monosaccharides such as $D-GlcNSO_3-6OSO_3$ and $IdoA_2OSO_3$ which are often found in sulfated glycosaminoglycans, such as heparin sulfate and dermatin sulfate.

2. Phosphorylated or sulfated oligosaccharides. This includes O- and N-sulfate oligosaccharides derived from hydrolysis of glycosaminoglycans (GAGS) and proteoglycans. Sulfated GAGs of physiological significance include dermatan sulfate, chondroitin sulfate, heparin sulfate, and keratan sulfate. Oligosaccharides derived from heparin sulfate are of particular importance because of their anti-blood clotting activity. Phosphorylated oligosaccharides include those derived from several bacterial lipopolysaccharides. An example is alpha-L-Colp-(1→2)-beta-D-Galp-(1→3)-[alpha-L-Colp-(1→4)]-beta-D-GlcpNAc, containing a 4,6-cyclic phosphate in the galactose residue. This is a phosphorylated oligosaccharide corresponding to *Vibrio cholerae* O139 polysaccharide. C-glycoside ketones and C-glycoside keto-amide derivatives are readily prepared from these oligosaccharides in aqueous-based conditions and without the loss of the phosphate or sulfate groups.

3. RNA- and DNA-derived oligonucleotides (aptamers). Oligonucleic acids that lack the N-linked base on the 3'-end, i.e. that terminate in a free ribose (for RNA oligos) or 2-deoxyribose (for DNA oligos) can be used to prepare C-glycoside ketones and C-glycoside keto-amide derivatives using the techniques described herein. The C-glycoside keto-amide derivative chemistry is particularly applicable to labile RNA oligonucleotides The reaction to make the sugar C-glycoside ketone reactant used herein has been described previously in applicant's co-pending application Ser. No. 11/899,180, filed Sep. 5, 2007 and entitled "Preparation and Uses of Locked Ring Sugar C-Glycoside Derivatives" (the contents of which are incorporated by reference herein). In brief, the aldose reducing sugar is contacted with a β-diketone under conditions and for a period of time effective to form a C-glycoside ketone. The reaction of the aldose sugars with the β-diketone to synthesize the C-glycoside ketone Synthesis is preferably performed in a buffered aqueous solvent. The precise conditions are somewhat variable and may be readily selected by the skilled user. By way of example, and without being limited thereto, in the preferred embodiment, the sugar is dissolved in aqueous buffer, such as sodium bicarbonate solution (38 g/L) to give a final concentration of sugar of 50 mg (0.28 mmoles) per mL. It is understood that other buffers such as potassium bicarbonate, sodium carbonate, or potassium carbonate may also be used. The pH may range from approximately 8-10, and is typically pH 8.2. A slight molar excess of acetylacetone (also called 2,4-pentanedione) is added, to typically give a final concentration of 35 mg (0.35 mmoles) per mL of buffer. Other 2,4-diketones may also be used in place of the acetylacetone, such as asymmetric 2,4-diketone or halogenated 2,4-diketones such as 1,1,1-trifluoro-2,4-pentanedione, or 1,1,1,5,5,5-hexfluoro-2,4-pentadione. The quantity of the 2,4-diketone relative to the sugar is not critical and may be increased without adversely affecting the yield of the C-glycoside ketone. The reaction may be conducted with or without heating, in any convenient reaction vessel. In one embodiment, the reaction is heated in a sealed tube, or in scaled up reactions is heated under reflux with stirring. The temperature for the synthesis may range from approximately 10-99° C. Typically, approximately 80-90° C. is preferred with a reaction time of 4 hours. However, lower temperatures are still effective but may simply require longer reaction times, and they may even be preferred for reactions involving labile sugars.

In accordance with this reaction, if the β-diketone is represented by the formula:

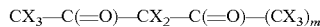

wherein m is an integer greater than or equal to one, but is preferably 1 or 2, and Y at any of the noted positions is independently selected from H and a halogen, the —$CY_2$— between the ketones is acidic and reacts with the C1 of the anomeric residue of the sugar. The resultant "locked ring sugar" C-glycosidic ketone may then be shown as:

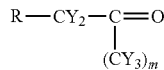

wherein R is a saccharide. Acetic acid (or $(CY_3)_m$—COOH) is also released in the reaction. More specifically, R is:

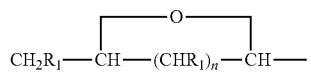

wherein n and $R_2$ are as described in the general structure for the aldose reducing sugar described above. Thus, in this formula, n is 2 or 3, and $R_2$ at any of the C2, C3, C4, C5, and C6 carbons for n equal to 3, or at any of the C2, C3, C4, and C5 carbons for n equal to 2, are independently selected from the group consisting of hydroxyls, amines, O-acyls, N-acyls, acid moieties, carboxylates, phosphates, sulfates, N-acetates, O-acetates, O-pyruvates, O-alkyls, and glycosidically-linked sugars.

As will be described in greater detail hereinbelow, the reactions to produce the acyl-linked ketone reactive compound and the final product, the C-glycoside keto-amide derivative, are preferably conducted in the same reaction vessel used to produce the C-glycoside ketone, thereby eliminating the need to isolate or separate the C-glycoside ketone before proceeding. However, after cooling, the C-glycoside ketone may be recovered and substantially purified from the reaction solution if desired. For example, the reaction solution may first be optionally extracted with ethyl acetate or other water-immiscible solvent in order to recover any excess 2,4-diketone. The bicarbonate (or carbonate) in the aqueous phase may be neutralized to approximately pH 7 by addition of sufficient strong cation exchange resin (typically Dowex 50 W). After removing the spent Dowex resin by filtering or allowing it to settle out, the C-glycoside ketone product can be recovered from the aqueous reaction medium by evaporation or drying. The C-glycoside ketone products are sufficiently pure (MALDI-TOF MS, NMR, GC-MS, TLC) so as not to require any chromatographic cleanup. This reduces the cost of production considerably, and indicates that scale-up to Kg quantities or greater will not present a major problem.

The acyl-linked ketone reactive compound used for producing the C-glycoside keto-amide derivatives of the invention may be prepared by contacting the lipid with a ketone reactive compound under conditions and for a period of time effective to produce the acyl-linked ketone reactive compound. Without being limited thereto, preferred ketone reactive compounds for use herein include hydrazines ($H_2N.NH_2$) or their salts, hydrazides ($H_2N.N$—C(=O)R), hydroxylamines ($H_2NOH$), amines, and semicarbazides (HC=NNHC(=O)$NH_2$). Hydroxylamines and hydrazine salts, such as hydrazine hemisulfate or hydrochloride, are particularly preferred, and are preferred over hydrazine due to their low cost and ease of handling. However, when using hydroxylamines it is preferred to protect the amine group to ensure formation of the acyl β-hydroxylamine and prevent formation of an acyl N-hydroxylamine (by reaction between the amine group and the carboxyl group of the fatty acid). Acyl N-hydroxylamines are not reactive with ketones. The amine may be deprotected following formation of the acyl O-hydroxylamine. For example, a typical formation of acyl O-hydroxylamines may involve acylation of N-hydroxyphthalamide followed by de-protective removal of the phthalamide group by the Ing-Manske reaction. It is also envisioned that thiols may be used, although they are not desirable due to their accompanying odor. The specific acyl-linked ketone reactive compound produced will of course vary with the lipid and ketone reactive compound used. When reacted with the fatty acids within the lipids, the hydrazines (or their salts) and hydrazides each form an acyl-hydrazide, hydroxylamines form acyl-O-hydroxylamines, amines form acyl-amines, and semicarbazides form acyl-semicarbazides. When produced as described above, the acyl-linked ketone reactive compound (and specifically the acyl hydrazide or O-hydroxylamine) is of the formula:

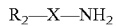

wherein X is O or NH and $R_2$ is an acyl moiety derived from any lipid fatty acid, and as such may also be shown as —C(=O)—$R_3$ wherein $R_3$ is a C5 to C22 straight or branched chain hydrocarbon which may be saturated or unsaturated, and may be optionally substituted. By way of example, in a preferred embodiment, the reaction of a plant lipid of the general formula $R_3$—COOR$_x$ as described above with hydrazine sulfate will produce a fatty acid (acyl) hydrazide and glycerol as follows:

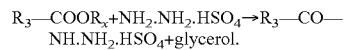

For preparation of the acyl-linked ketone reactive compounds, the lipids are dissolved or suspended in an aqueous solution or slurry and contacted with the ketone reactive compound. Ethanol may be added to facilitate formation of the slurry. Preparation of the ketohydrazone requires approximately a molar equivalence or a slight molar excess of the hydrazine or other ketone reactive compound. In a preferred embodiment, when reacting triglycerides or other fatty acid esters, the reaction rate may be significantly increased by addition of NaOH and lipase enzyme. The source of the lipase is not critical. The lipid and ketone reactive compound are reacted, preferably with agitation or stirring, for approximately 25-100° C. for approximately 1-4 days. The precise reaction time will vary with the lipid source and the presence or absence of lipase. By way of example and without being limited thereto, when reacting vegetable oil with hydrazine hemisulfate in the presence of lipase at approximately 35° C., a reaction time of approximately 72 hours is typical. If necessary any excess hydrazine or other ketone reactive reagent can be removed by extraction with a water-immiscible ketone such as 1-heptanone or methyl isobutyl ketone (MIBK). The resultant acyl-linked ketone reactive compound is typically recovered in near-quantitative yield by evaporation of the aqueous reaction mixture.

As with the C-glycoside ketone, the resultant acyl-linked ketone reactive compound may also be recovered as described above, and subsequently contacted with the C-glycoside ketone to produce the desired C-glycoside keto-amide derivative. However, in a preferred embodiment, the reaction to produce the acyl-linked ketone reactive compound is conducted in the same reaction vessel containing the C-glycoside ketone, in a so-called "one pot" reaction. In this latter embodiment, as the resultant acyl-linked ketone reactive compounds are formed they will react with the C-glycoside ketones already present in the reaction vessel.

In either embodiment, the reaction of the C-glycoside ketone with acyl-linked ketone reactive compound to produce C-glycoside keto-amide derivative is conducted in an aqueous solvent without any required catalysts. An alcohol such as methanol and/or ethanol may be added to facilitate solution formation. The temperature is not critical and may vary between about 10 and 99° C., preferably about 50° C. with agitation. The reaction time is relatively short, and the reaction may be completed in approximately 2 to 4 hours. As above, if necessary any excess acyl-hydrazide or other acyl-linked ketone reactive reagent can be removed by extraction with a water-immiscible ketone such as 1-heptanone or methyl isobutyl ketone (MIBK). The resultant C-glycoside keto-amide derivative may be recovered by evaporation of the aqueous reaction mixture.

The C-glycoside keto-amide derivative produced by the reaction of the C-glycoside ketone and acyl-linked ketone reactive compound is of the formula:

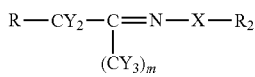

wherein R, Y, m, X and $R_2$ are as described above. When using the general structure for the aldose reducing sugar described above, R may also be shown by the formula:

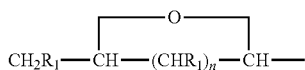

wherein:

n is 2 or 3; and $R_1$ at any of the C2, C3, C4, C5, and C6 carbons for n equal to 3, or at any of the C2, C3, C4, and C5 carbons for n equal to 2, are independently selected from the group consisting of hydroxyls, amines, O-acyls, N-acyls, acid moieties, carboxylates, phosphates, sulfates, N-acetates, O-acetates, O-pyruvates, O-alkyls, and glycosidically-linked sugars.

By way of example and without being limited thereto, the reaction of a C6 aldose sugar to produce a C-glycoside ketone, which is then reacted with a acyl hydrazide or O-hydroxylamine of the formula $R_2$—X—$NH_2$ (wherein X is O or NH and $R_2$ is an acyl moiety derived from any lipid fatty acid) to produce a C-glycoside keto-amide derivative, may be shown by the reaction scheme:

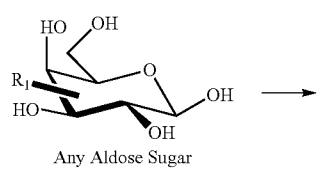

Any Aldose Sugar

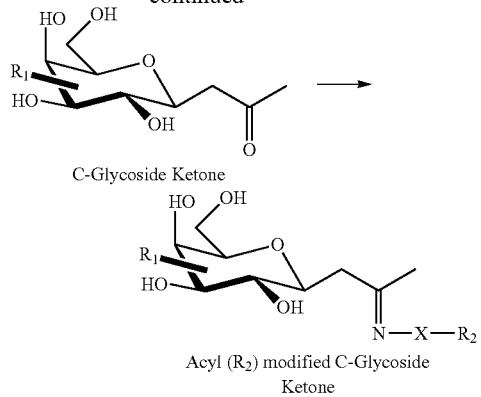

C-Glycoside Ketone

Acyl ($R_2$) modified C-Glycoside Ketone wherein the C-glycoside keto-amide derivative is a hydrazone when X is N and an oxime when X is O.

In accordance with an alternative embodiment, the C-glycoside keto-amide derivatives of the invention, specifically acyl C-glycoside ketohydrazones, may be prepared by a first reaction of the C-glycoside ketone with hydrazine or a salt thereof to produce a C-glycoside hydrazide. This C-glycoside hydrazide is then reacted with the lipid to produce the C-glycoside keto-amide derivative. The first reaction may be conducted by contacting the C-glycoside ketone and hydrazine or its salt in an aqueous medium under conditions similar to those described for the reaction of C-glycoside ketone and acyl-linked ketone reactive compound to produce C-glycoside keto-amide derivative as described above. However, the reaction is preferably conducted under conditions of reductive amination to chemically reduce the N of the hydrazine which is bonded to or reacted at the site of the ketone moiety on the C-glycoside ketone. Reductive amination may be effected simultaneously with or following completion of the first reaction, by addition of reducing agents conventional in the art. A variety of reducing agents are suitable for use herein, and include but are not limited to Zn/HCl, Na borohydride, or Na cyanoborohydride, with Zn/HCl preferred due to their low cost.

The C-glycoside hydrazide produced above may then be contacted with the fatty acid containing lipid, which again may be free fatty acid, its salts, fatty acid esters and/or triglycerides, under aqueous conditions, to form an acyl C-glycoside ketohydrazone. Typical conditions for this reaction are 50° C. for 2-4 h, optionally catalyzed by NaOH and/or lipase.

By way of example and without being limited thereto, in accordance with this alternative embodiment, the reaction of a C-glycoside ketone with hydrazine to produce a C-glycoside hydrazide, which is then reacted with a lipid to produce a C-glycoside ketohydrazone, may be shown by the reaction scheme:

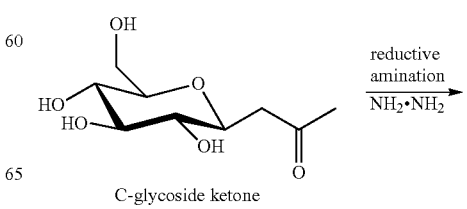

C-glycoside ketone

-continued

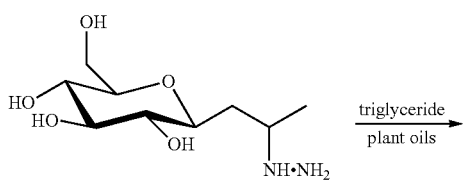

C-glycoside ketohydrazide

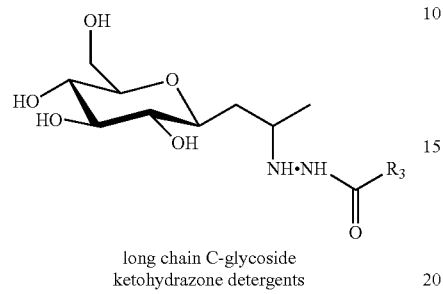

long chain C-glycoside
ketohydrazone detergents wherein $R_3$ is defined as described above.

The C-Glycoside keto-amide derivatives of this invention exhibit excellent detergent properties. An effective detergent needs a water-soluble head group (i.e., the sugar part) and an oil-soluble lipid tail. The length of the tail determines how easily the detergent forms micelles (the critical micelle concentration, CMC), longer tails giving detergents with lower CMC values. The head group determines whether the detergent is 1. non-ionic, 2. anionic, or 3. Cationic. Representative examples of these different classes of detergents which may be produced in accordance with this invention include the following:

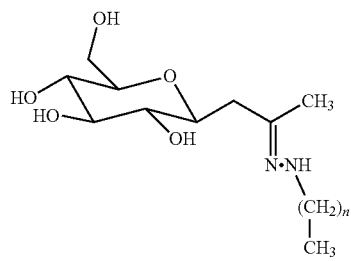

Non-ionic type
Glucose-C-glycoside
ketohydrazone

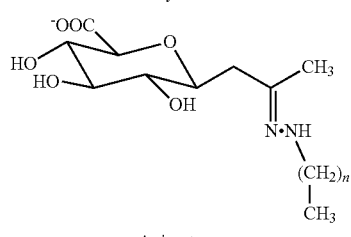

Anion type
Glucuronic-C-glycoside
ketohydrazone

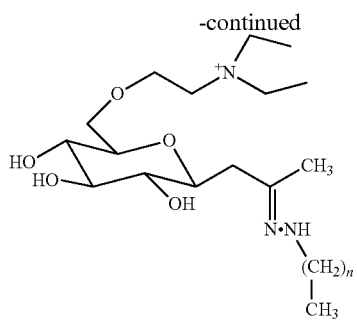

Cationic type
DEAE-Glucose-C-glycoside
ketohydrazone

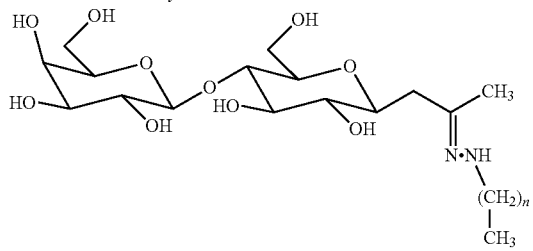

Disaccharide type
Lactose-C-glycoside
ketohydrazone

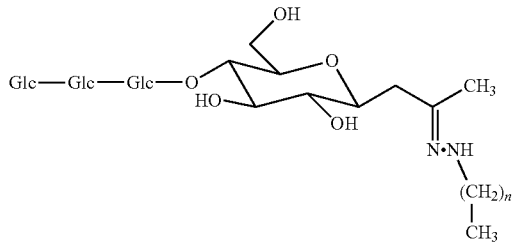

Oligosaccharide type
Maltotetraose-C-glycoside
ketohydrazone

By way of example and without being limited thereto, preferred anionic detergents may be based on uronic acid C-Glycoside keto-amide derivatives. Anionic sugars (e.g., glucuronic acid, phosphoglucose, pectin-based sugars) may be converted into C-glycoside in excellent yields. These may then be readily converted into their corresponding C-Glycoside keto-amide derivatives. Current anionic detergents (e.g., lauryl sulfate) are very high-foam surfactants found in shampoos and laundry detergents. The highly polar head allows the molecule to bond with polar molecules such as water. Non-limiting examples of preferred non-ionic detergents may be based on neutral C-Glycoside keto-amide derivatives. Neutral sugars (e.g., glucose, xylose, galactose, disaccharides, oligosaccharides) may be readily converted into C-Glycoside keto-amide derivatives with non-ionic detergent properties. Non-ionic detergents are generally low-foaming, and find uses as dishwasher detergents and in pharmaceuticals. Cationic detergents (e.g., cetrimide) tend to be higher cost and are used as topic antiseptics, and may be found in many household products such as shampoos and cosmetics. Examples of preferred cationic detergents include but are not limited to C-Glycoside Keto-amide derivatives prepared from amino sugars such as DEAE-glucose, glucosamine, or chitin sugars.

The C-glycoside ketone and fatty acid hydrazide starting ingredients, and the C-Glycoside keto-amide derivative detergents may be classified as being environmentally friendly. They are made from renewable agricultural starting materials (lipids and sugars), and require only mild, water-based chemistry. They are also phosphate-free, and potentially biodegradable. The anionic-type, made from uronic acids, give a stable high-foam that is superior to the AHPs, and have considerable potential as a new class of general anionic detergents.

The following examples are intended only to further illustrate the invention and are not intended to limit the scope of the invention which is defined by the claims.

Example 1

Using the chemistry described above fatty acid hydrazides have been prepared directly from commercial olive oil, commercial sesame oil, and commercial corn oil. These natural plant triglycerides therefore gave stearic hydrazide, oleic hydrazide, and palmitic hydrazide. These have been analyzed by MALDI-TOF mass spectrometry giving rise to sodium adduct [M+Na]$^+$ molecular ions. All of these conversions were essentially quantitative. The stearic hydrazide, oleic hydrazide, and palmitic hydrazide, generated from commercial plant oils have been reacted with C-glycoside ketones made from glucose, lactose, and glucuronic acid using the methods described above. The authenticity of the products, long chain acyl C-glycoside ketohydrazones, has been shown by MALDI-TOF MS analysis. The yields for this final step were also essentially quantitative.

General Procedure to Form Hydrazides from Vegetable Oil:

Sesame oil (2.0330 g) and *Candida antarctica* lipase (1.0380 g) were weighed out into an Erlenmeyer flask. Ethanol (3.0 mL) was then added to make a slurry which was placed on an orbital shaker at 200 rpm and 28° C. for 24 hours.

Prior to removing lipase slurry from the orbital shaker, hydrazine hemisulfate (2.7993 g, 34.5 mmol) was dissolved in water (20 mL) and cooled in an ice bath. To the cool solution, sodium hydroxide pellets (1.3843 g, 34.6 mmol) were added and the mixture stirred to completely dissolve the pellets. Ethanol (30 mL) was added to precipitate sodium salt impurities which were removed by vacuum filtration. The hydrazine filtrate was retained.

The lipase/sesame oil slurry was filtered through a BD 5 mL leur-lock syringe with a Millex-SR 0.5 µm filter syringe and added directly into the hydrazine solution. A fine precipitate formed almost immediately. The mixture was placed on an orbital shaker at 200 rpm and 35° C. for 72 hours. The solution was cooled to approximately 10° C. and the precipitate was filtered, collected, and dried under vacuum overnight to give a soapy lightly yellow solid. The acetone and 3-heptanone hydrazone derivatives were prepared and analyzed by MALDI-TOF-MS.

General Procedure for the C-Glycoside Formation:

D-glucose (0.0735 g, 0.408 mmol) was dissolved in sodium bicarbonate buffer (2 mL). 2,4-Pentanedione (750 µL, 7.30 mmol) was added and the reaction was heated at 80° C. (4 h) with occasional vortexing. The solution was allowed to cool to room temperature and extracted with EtOAc (2×2 mL); the organic layer was removed. To the aqueous layer, Dowex-50W strong cation exchange resin (ca 5 mL) was added and agitated by hand. The resin was removed by filtration and the filtrate was analyzed by MALDI-TOF-MS.

General Procedure for the C-Glycoside Hydrazone Formation:

Lauric hydrazide (0.0293 g, 0.137 mmol) was added to dried glucose-C-glycoside ketone (0.0631 g, 0.269 mmol). The mixture was dissolved in 2 mL 1:1 MeOH/EtOH with vortexing and heat to 50° C. for 4 hours. After cooling, the samples were concentrated to dryness and analyzed by MALDI-TOF-MS for product.

It is understood that the foregoing detailed description is given merely by way of illustration and that modifications and variations may be made therein without departing from the spirit and scope of the invention.

I claim:

1. A C-glycoside keto-amide derivative of the formula:

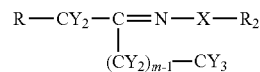

wherein:
R is a saccharide;
Y is independently selected from H or a halogen;
m is an integer greater than or equal to 1;
X is O or NH; and
$R_2$ is an acyl of the formula —C(O)—$R_3$ wherein $R_3$ consists of a C5 to C22 straight or branched chain hydrocarbon, which is saturated or unsaturated.

2. The C-glycoside keto-amide derivative of claim 1 wherein X is O.

3. The C-glycoside keto-amide derivative of claim 1 wherein m is 1 or 2.

4. A C-glycoside keto-amide derivative of the formula:

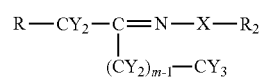

wherein R is:

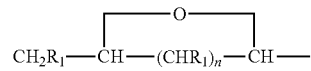

and further wherein:
n is 2 or 3;
$R_1$ at any of the C2, C3, C4, C5, and C6 carbons for n equal to 3, or at any of the C2, C3, C4, and C5 carbons for n equal to 2, are independently selected from the group consisting of hydroxyls, amines, O-acyls, N-acyls, acid moieties, carboxylates, phosphates, sulfates, N-acetates, O-acetates, O-pyruvates, O-alkyls, and glycosidically-linked sugars;
Y is independently selected from H or a halogen;
m is an integer greater than or equal to 1;
X is O or NH; and
$R_2$ is an acyl of the formula —C(O)—$R_3$ wherein $R_3$ consists of a C5 to C22 straight or branched chain hydrocarbon, which is saturated or unsaturated.

5. The C-glycoside keto-amide derivative of claim 4 wherein X is O.

6. The C-glycoside keto-amide derivative of claim 4 wherein n is 3.

7. A method for producing a C-glycoside keto-amide derivative comprising reacting a C-glycoside ketone with an acyl-linked ketone reactive compound under conditions and for a period of time effective to produce a C-glycoside keto-amide derivative, wherein said C-glycoside ketone is of the formula:

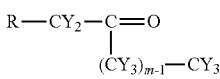

said acyl-linked ketone reactive compound is of the formula:

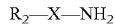

and said C-glycoside keto-amide derivative is of the formula:

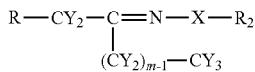

wherein:
R is a saccharide;
Y is independently selected from H or a halogen;
m is an integer greater than or equal to 1;
X is O or NH; and
$R_2$ is an acyl of the formula —C(O)—$R_3$ wherein $R_3$ consists of a C5 to C22 straight or branched chain hydrocarbon, which is saturated or unsaturated.

8. The method of claim 7 wherein said acyl-linked ketone comprises an acyl hydrazine, and said C-glycoside keto-amide derivative which is produced comprises a C-glycoside keto-hydrazone.

9. The method of claim 7 wherein said acyl-linked ketone comprises an acyl O-hydroxylamine, and said C-glycoside keto-amide derivative which is produced comprises a C-glycoside keto-oxime.

10. The method of claim 7 wherein said reacting is under aqueous conditions.

11. The method of claim 7 further comprising reacting a lipid with a ketone reactive compound under conditions and for a period of time effective to produce said acyl-linked ketone reactive compound.

12. The method of claim 11 wherein said lipid is selected from group consisting of free fatty acids or their salts, fatty acid esters, triglycerides, plant oils, animal fats, and mixtures thereof.

13. The method of claim 7 further comprising reacting an aldose reducing sugar with a β-diketone under conditions and for a period of time effective to form said C-glycoside ketone, which said aldose reducing sugar comprises an aldehyde containing hexose aldose reducing sugar or an aldehyde containing pentose aldose reducing sugar, wherein said hexose is optionally substituted at one or more of the C2, C3, C4, C5, and C6 positions thereof and said pentose is optionally substituted at one or more of the C2, C3, C4, and C5 positions thereof.

14. A method for producing a C-glycoside keto-hydrazone derivative comprising:

a. reacting a C-glycoside ketone with hydrazine or a salt thereof under conditions and for a period of time effective to produce a C-glycoside hydrazide; and
b. reacting said C-glycoside hydrazide with a lipid under conditions and for a period of time effective to produce a C-glycoside ketohydrazone;

wherein said C-glycoside keto-hydrazone is of the formula:

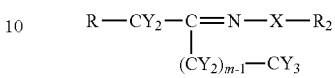

wherein:
R is a saccharide;
Y is independently selected from H or a halogen;
m is an integer greater than or equal to 1;
X is NH; and
$R_2$ is an acyl of the formula —C(O)—$R_3$ wherein $R_3$ consists of a C5 to C22 straight or branched chain hydrocarbon, which is saturated or unsaturated.

15. The method of claim 14 wherein said reacting said C-glycoside ketone with said hydrazine or a salt thereof to produce said C-glycoside hydrazide is under reductive amination conditions.

16. The method of claim 14 wherein said reacting to produce said C-glycoside hydrazide comprises:
a. reacting said C-glycoside ketone with hydrazine or a salt thereof under conditions and for a period of time effective to produce a C-glycoside hydrazone; and
b. reducing said C-glycoside hydrazone to said C-glycoside hydrazide.

17. The method of claim 14 wherein said lipid is selected from group consisting of free fatty acids or their salts, fatty acid esters, triglycerides, plant oils, animal fats, and mixtures thereof.

18. The C-glycoside keto-amide derivative of claim 1 wherein said $R_3$ is not substituted.

19. The C-glycoside keto-amide derivative of claim 4 wherein said $R_3$ is not substituted.

20. The method of claim 7 wherein said $R_3$ is not substituted.

21. The method of claim 14 wherein said $R_3$ is not substituted.

22. The C-glycoside keto-amide derivative of claim 1 wherein m is 1.

23. The C-glycoside keto-amide derivative of claim 4 wherein m is 1.

24. The method of claim 7 wherein m is 1.

25. The method of claim 16 wherein m is 1.

* * * * *